United States Patent [19]

Franchi

[11] Patent Number: 5,044,141

[45] Date of Patent: Sep. 3, 1991

[54] METHOD FOR STERILE PACKAGING AND WETTING OF ARTICLES

[76] Inventor: Richard M. Franchi, 264 Shagbark Dr., Derby, Conn. 06418

[21] Appl. No.: 551,066

[22] Filed: Jul. 11, 1990

[51] Int. Cl.$^5$ ............................................ B65B 55/028
[52] U.S. Cl. ........................................ 53/431; 53/440; 53/469; 206/205; 422/28; 422/294
[58] Field of Search ................. 53/127, 400, 401, 413, 53/425, 428, 431, 440, 469; 206/205, 210, 438; 422/28, 294; 604/304

[56] References Cited

U.S. PATENT DOCUMENTS

| | | | |
|---|---|---|---|
| 3,720,037 | 3/1973 | Jones | 53/431 X |
| 3,725,003 | 4/1973 | Moore et al. | 53/431 X |
| 3,754,368 | 8/1973 | Moore et al. | 53/431 |
| 3,857,677 | 12/1974 | Moore et al. | 53/431 X |
| 3,895,474 | 7/1975 | Bauer | 53/431 X |
| 4,099,914 | 7/1978 | Gustafsson et al. | 53/431 X |
| 4,797,255 | 1/1989 | Hatanaka et al. | 422/28 |

FOREIGN PATENT DOCUMENTS 0054691 11/1987 Japan ................................ 53/425

*Primary Examiner*—John Sipos

[57] ABSTRACT

A method of sterile packaging and wetting articles within the package which involves the steps of partially filling a container with any of a number of anti-bacterial agents in liquid or semi-liquid form, then placing articles into the container, then sealing the container so that an air space is formed above the liquid within the container, then heating the container and its contents to a temperature substantially below the boiling point of the liquid, and at a pressure of about one atmosphere, until the surfaces within the container above and below the liquid level, and the entire contents of such container, are sterilized, and finally cooling the container and its contents to a temperature at or below the dew point of the air space until the surfaces within the container and above the liquid level are wetted by the condensed liquid from the air.

23 Claims, No Drawings

METHOD FOR STERILE PACKAGING AND WETTING OF ARTICLES

BACKGROUND OF THE INVENTION

U.S Pat. No. 3,618,283 disclosed a method for the sterile packaging of surgical sponges and other articles in sealed flexible wrappers. During the packaging operation and immediately following the sealing of the wrappers, each package is squeezed or compressed so that all of the surfaces within the packages will be flushed or wetted by the germicidal soap solution contained within the package. Subsequent heating of the package at a low enough temperature to avoid rupturing the flexible walls of the wrapper results in sterilization of all the surfaces contacted by the liquid or, in other words, all of the surfaces within the package.

U.S. Pat. Nos. 3,857,677 and 3,725,003 claim to be an improvement over U.S. Pat. No. 3,618,283 because there is no need to flush or wet the surfaces within the package in order to obtain sterilization. The Patents that claim to be an improvement in this case rely only on heating the contents of the sealed package, including the anti-bacterial agent to a temperature substantially below the boiling point to obtain complete sterilization of the inner surfaces of the package.

SUMMARY OF THE INVENTION

The main aspect of this invention concerns the manner in which all surfaces inside a package are to be wetted by anti-bacterial agents after being sterilized by the processes disclosed in U.S. Pat. Nos. 3,857,677 and 3,725,003. Because there is no wetting or flushing of objects in the package disclosed in these two Patents, parts of the objects may be dry after the sterilization process. These objects may be required to be wetted on all surfaces so that substantial amounts of antibacterial agent can be transferred from the object to the surface to be cleaned or coated during application on the skin or other desired areas.

The invention in this application involves the steps of first partially filling a bottle, bag, or other sealable container with a solution, usually but not necessarily an aqueous solution, of a standard anti-bacterial agent (some standard anti-bacterial agents are solutions of iodine (iodofor), halogenated bis-phenols such as hexachlorophene, quaternary ammonium salts such as benzalkonium chloride, and sodium ethylmercurithiosalicylate). After partially filling the container with such a solution, and after placing in the container those items to be sterilized, the container is sealed so that an air (or gas) space is disposed above the liquid. Thereafter the container and its contents are heated to a temperature well below the boiling point of the liquid and at a pressure of about one atmosphere. In general the temperature to which the container and its contents are heated to will fall within the range of about 115 to 210degrees F°, but usually below 180 degrees F°, the particular temperature selected depending upon the anti-bacterial agent used and the duration of the heating step. The heating operation is continued until all organisms, including spores, are killed, the interval normally falling within the range of 2 to 48 hours. Finally, the container and its contents are cooled to below the dew point of the air (or gas) so as to allow the humidified air (or gas) to condense the solution on to the surfaces inside the container which are in the air space and not submerged under the liquid solution. The cooling operation depends upon the heating operation because the dew point temperature is relative to the humidity and temperature of the air (or gas) in the space which is created by the heated air (or gas).

DESCRIPTION OF THE INVENTION

Some methods of the sterilization process and anti-bacterial agents used in connection with the present invention have been disclosed in U.S. Pat. Nos. 3,725,003 and 3,857,677.

The anti-bacterial agents used in connection with the present method are conventional. Of the numerous agents known to have anti-bacterial properties and which are believed suitable for use in connection with the invention, several have been previously disclosed in the aforementioned U.S. Patents. On the basis of this previous disclosure of anti-bacterial agents, it is believed that the following general conditions are applicable.

Where the anti-bacterial agent is sodium etylmercurithiosalicylate in aqueous solution, a concentration within the range of 1:100 to 1:2000 has been found effective. The heating step should exceed 12 hours at a temperature within the range of about 160 to 210 degrees F° and then a cooling step should be at a temperature below 60 degrees F° for at least 4 hours.

For hexachlorophene, a halogenated2,2'-bis-phenol, the aqueous solution should have a concentration within the range of about 0.25 to 4.0 percent. The container and its contents should be heated at a temperature within the range of about 160 to 10 degrees F° for an interval exceeding 12 hours then cooled to a temperature below 60 degrees F° for at least 4 hours.

Quateranary ammonium surface-active disinfectants have also been found effective. Thus, benzalkonium chloride in aqueous solution having a concentration falling within the range of 0.0025 to 0.2 percent may be used. The temperature of the heating step should fall within the range of about 150 to 210 degrees F° for an interval exceeding 12 hours then cooled to below 60 degrees F° for a period of at least 4 hours.

Iodine preparations or complexes which liberate free iodine in aqueous solution are highly effective for use in connection with the method of this invention. An aqueous iodophor solution having an iodine concentration within the range of 0.0012 to 3.0 percent is suitable. The heating step should be at a temperature of between 115 and 150 degrees F° for a period in excess of 2 hours then cooled to below 60 degrees F° for a period exceeding 4 hours.

Sterilization occurs during the heating cycle. The coating (or wetting)of the surface portions above the liquid solution occurs during the cooling cycle. Normally, the space above the liquid in the container will befilled with air; however other gases might be substituted if desired.

Some of the specific applications for the operative procedure are detailed in the following examples;

EXAMPLE I

An aqueous solution of a quaternary ammonium salt with a concentration of about 1:750 partially fills a flexible container and then a swabstick is placed in the container. The container is then sealed and an air space is formed above the liquid in the container. The container and its contents are then heated to 170 degrees F° for 24 hours. The container and its contents are then cooled to 60 degrees F° for 4 hours.

EXAMPLE II

An aqueous solution of liquid hexachlorophene with a concentration of 3.0 percent partially fills a flexible container and then a swabstick is placed in the container. The container is then sealed and an air space is formed above the liquid in the container while the swabstick remains partially in the air space. The container and its contents are then heated to 175 degrees F° for 24 hours. The container and its contents are then cooled to 60 degrees F° for 4 hours.

EXAMPLE III

An aqueous solution of sodium ethylmercurithiosalicylate with a concentration of 1:1000 partially fills a flexible container and then a swabstick is placed in the container. The container is then sealed and an air space is formed above the liquid in the container while the swabstick remains partially in the air space. The container and its contents are then heated to 175 degrees F° for 24 hours while maintaining a pressure of about one atmosphere. The container and its contents are then cooled to 60 degrees F° for 4 hours.

BEST MODE OF THE INVENTION

An aqueous solution of an iodophor which results in a solution having a 0.23 percent of free iodine partially fills a flexible container and then a sponge is placed in the container. The container is then sealed and an air space is formed above the liquid in the container while the sponge remains partially in the air space. The container and its contents are then heated to 140 degrees F° for 24 hours while maintaining a pressure of about one atmosphere. The container and its contents are then cooled to a temperature of 60 degrees F°.

It should be noted that all examples and best mode contain a total of 90 milliliters (ml) of liquid solution for each container.

Also noted is the fact that the anti-bacterial solutions can contain soap in the aqueous solution.

While in the foregoing I have disclosed the method of the invention in considerable detail for the purposes of illustration, it will be understood by those skilled in the art that many of the details may be varied without depating from the spirit and scope of the invention.

What is claimed is:

1. A method of sterile packaging and wetting of articles comprising the sequential steps of partially filling a container with a solution of a standard anti-bacterial agent; then placing an article in the container so that the article is partially above the solution; then sealing said container to provide a gas space above the solution within the sealed container; then heating said container and its contents to a temperature substantially below the boiling point of the solution and at a pressure of about one atmosphere until all the surfaces inside the container above and below the solution, and the entire contents of the container, are sterilized; and thereafter cooling the container and its entire contents to a temperature at which condensation occurs on the surfaces inside the container that are above the solution until condensation occurs.

2. The method of claim 1 in which the anti-bacterial agent is selected from the group consisting of iodophor, sodium ethylmercurithiosalicylate, quartenary ammonium salts, and halogenated bis-phenols.

3. The method of claim 2 in which the container and its contents are heated to a temperature within the range of 120° to 210° F.

4. The method of claim 2 in which the gas space contains air.

5. The method of claim 2 in which the container and its contents are heated to a temperature within the range of 130° to 150° F. for at least 2 hours.

6. The method of claim 1 in which the solution is standard anti-bacterial agent having an available iodine concentration within the range of 0.0012 to 3.0 percent.

7. The method of claim 6 in which the container and its contents are heated to a temperature within the range of 120° to 150° F.

8. The method of claim 1 in which the solution is an aqueous solution of a halogenated 2,2'-bis-phenol having a concentration within the range of 0.25 to 4.0 percent.

9. The method of claim 1 in which the solution is an aqueous solution of a quaternary ammonium salt having a concentration within the range of 0.0025 to 0.2 percent.

10. The method of claim 1 in which the solution is a solution of sodium ethylmercurithiosalicylate having a concentration within the range of 1:100 to 1:2000.

11. The method of claim 2 in which the solution contains soap.

12. A method of sterile packaging and wetting of articles comprising the steps of partially filling a container with a solution of a standard anti-bacterial agent and placing articles in the container, then sealing said container to provide a gas space above the solution within the sealed container; then heating said container and its contents to a temperature substantially below the boiling point of the solution and at a pressure of about one atmosphere until all the surfaces inside the container above and below the solution, and the entire contents of the container, are sterilized; and thereafter cooling the container and its entire contents to a temperature at which condensation occurs on the surfaces inside the container that are above the solution until condensation occurs.

13. The method of claim 12 in which the anti-bacterial agent is selected from the group of iodophor, sodium ethylmercurithiosalicylate, quaternary ammonium salts, and halogenated bis-phenols.

14. The method of claim 13 in which articles placed in the container are completely above the liquid level of the solution.

15. The method of claim 12 in which the container and its contents are heated to a temperature within the range of 120° to 210° F.

16. The method of claim 12 in which the gas space contains air.

17. The method of claim 12 in which the container and its contents are heated to a temperature within the range of 130° to 150° F for at least 2 hours.

18. The method of claim 12 in which the solution is a standard anti-bacterial agent having an available iodine concentration within the range of 0.0012 to 3.0 percent.

19. The method of claim 18 in which the container and its contents are heated to a temperature within the range of 120° to 150° F.

20. The method of claim 12 in which the solution is an aqueous solution of a halogenated 2,2'-bis-phenol having a concentration within the range of 0.25 to 4.0 percent.

21. The method of claim 12 in which the solution is an aqueous solution of a quaternary ammonium salt having a concentration within the range of 0.0025 to 0.2 percent.

22. The method of claim 12 in which the the solution is a solution of sodium ethylmercurithiosalicylate having a concentration within the range of 1:100 to 1:2000.

23. The method of claim 13 in which the solution contains soap.

* * * * *